United States Patent [19]

Nachman et al.

[11] Patent Number: 5,795,857
[45] Date of Patent: Aug. 18, 1998

[54] MIMETIC INSECT PYROKININ ANALOGS FOR INSECT CONTROL

[75] Inventors: Ronald J. Nachman, Willis, Tex.; Peter E. A. Teal, Gainesville, Fla.; Grant Mark Holman, Bryan, Tex.

[73] Assignee: The United States of America as represented by the Secretary of the Agriculture, Washington, D.C.

[21] Appl. No.: 700,915

[22] Filed: Aug. 22, 1996

[51] Int. Cl.$^6$ .............................. A01N 37/18; A61K 38/28
[52] U.S. Cl. ..................... 514/2; 514/16; 514/17; 514/18; 514/21; 530/300; 530/323; 530/329; 530/330; 530/345; 530/858
[58] Field of Search ........................ 530/300, 323, 530/329, 330, 345, 858; 514/2, 16, 17, 18, 21

[56] References Cited

U.S. PATENT DOCUMENTS 5,032,576  7/1991  Raina et al. ............................ 514/12

OTHER PUBLICATIONS

Chemical Abstracts 125:159037, "Potent Pheromonotropic/Myotropic Activity of a Carboranyl Pseudopeptide Analog of the Insect Pyrokinin/PBAN Neuropeptide Family", 1996.
Chemical Abstracts 123:139491, "Pseudopeptides of the Pyrokinin/PBAN Insect Neuropeptide Family", 1995.

*Primary Examiner*—Frederick Krass
*Attorney, Agent, or Firm*—M. Howard Silverstein; Randall E. Deck; John D. Fado

[57] ABSTRACT

Novel pseudopeptide analogs of the insect pyrokinin neuropeptide family which possess biological activity mimicking that of the naturally occurring neuropeptides are disclosed. By addition of a hydrophobic moiety to an active portion of the pyrokinin peptides, analogs are produced which exhibit an overall amphiphilic nature and which are capable of penetrating the insect cuticle while still retaining biological activity. The analogs may be used for insect control by disrupting the reproductive, developmental, and/or digestive processes normally regulated by pryrokinins in insects.

22 Claims, 10 Drawing Sheets

Dose response of carborane pseudopeptide in *Heliothis virescens* as percent of amount produced with 5 pmol PBAN

FIG 4
Dose Response of Topically Applied Carborane Analog

MIMETIC INSECT PYROKININ ANALOGS FOR INSECT CONTROL

BACKGROUND OF THE INVENTION

1. Field of Invention

This invention relates to mimetic pseudopeptide analogs of the pyrokinin neuropeptide family, and the use of these analogs for insect control.

2. Description of the Prior Art

The pyrokinin family of insect neuropeptides is widespread in several insect orders and has been associated with a variety of different physiological functions (Schoofs et al., 1994, Structure function and distribution of insect myotropic peptides, In: *Perspectives in Comparative Endocrinology*, Davey et al. eds., Ottawa: National Research Council of Canada, pp. 155–165). Although the first pyrokinin, leucopyrokinin (LPK) was originally identified as a hindgut and oviduct myotropin of the cockroach *Leucophaea maderae* (Holman et al., 1986, *Comp. Biochem. Physiol.*, 85:219–224), other members have since been isolated from other insect species on the basis of their ability to stimulate contractions of the oviduct of the locust (Schoofs et al., 1990, *Peptides*, 11:427–433; Schoofs et al., 1991, *Gen. Comp. Endocrinol.*, 81:97–104; Schoofs et al., 1990, *Insect Biochem.*, 20:479–484; Schoofs et al., 1993, *Comp. Biochem. Physiol.*, 106:103–109), sex pheromone biosynthesis in the corn earworm (Raina et al., 1989, *Science*, 244:796–798) and silkworm (Kitamura et al., 1990, *Agric. Biol. Chem.*, 54:2495–2497; and Kitamura et al., 1989, Biochem. Biophys. Res. Commun., 163:520–526), reddish coloration and melanization in silkworm larvae (Matsumoto et al., 1990, *J. Insect Physiol.*, 36:427–432) and diapause induction in silkworm moth eggs (Imai et al., 1991, *Proc. Jpn. Acad.* [B], 67:98–101). Among most species of Lepidoptera, the induction of sex pheromone biosynthesis is regulated by neuropeptides (PBAN) produced in the subesophageal ganglion (Raina, 1993, *Ann. Rev. Entomol.*, 38:329–349). Although the members of this class of insect neuropeptides vary from 8 to 34 amino acids in length (Schoofs et al., 1994, ibid), they share the common C-terminal pentapeptide Phe—X—Pro—Arg—Leu—NH$_2$ (X=Gly, Ser, Thr, Val) (Imai et al., ibid). The common C-terminal pentapeptide accounts for the considerable cross-activity observed for members of this family of peptides from diverse sources in the different physiological systems (Abernathy et al., 1995, *Peptides*, 16:215–219; Fonagy et al., 1992, *J. Insect Physiol.*, 38:651–657; Kuniyoshi et al., 1992, *Biosci. Biotech. Biochem.*, 56:167–168; Matsumoto et al., 1993, *J. Pestic. Sci.*, 18:127–129; Nachman and Holman, 1991, Myotropic insect neuropeptide families from the cockroach *Leucophaea Maderae*: Structure and Relationships, IN: *Insect neuropeptides: Chemistry, biology and action*, Menn et al. eds., Washington, D.C., American Cancer Society, pp. 194–214; and Nachman et al., 1993, *Peptides*, 14:1043–1048).

Studies on an active, rigid cyclic pyrokinin analog indicate that successful receptor interaction involves a β-turn over residues X—Pro—Arg—Leu—NH$_2$ of the C-terminal pentapeptide core (Nachman et al., 1993, *Biochem. Biophys. Res. Commun.*, 193:661–666; and Nachman et al., 1991, *Proc. Natl. Acad. Sci. USA*, 88:4518–4522). While this pentapeptide represents the active-core (minimum residue fragment) for biological activity in myotropic (Nachman et al., 1986, *Biochem. Biophys. Res. Commun.*, 137:936–942), pheromonotropic (Holman et al., 1991, *Insect Biochem.*, 21(1):107–112), melanization (Matsumoto et al., 1993, ibid) and diapause induction assays (Nachman et al., 1993, *Peptides*, 14:1043–1048), the observed potency is generally only a fraction of that of the respective parent pyrokinin peptide.

While members of the pyrokinin class of peptides can influence a number of physiological processes critical to insects, the structures of peptides pose several problems to their application and delivery for control techniques (Keeley et al., 1990, In *Insect Neurochemistry and Neurophysiology*, Borkovec and Masler eds., Humana, Clifton, N.J., pp. 163–203). The major limitations associated with the potential use of neuropeptides include their hydrophilic nature, which inhibits penetration through the insect cuticle, and that they can be subjected to rapid degradation by proteolytic enzymes in the lumen of the digestive tract when ingested, and in the hemolymph (blood). Some studies have been conducted to determine if ingested neuropeptides could pass through the gut wall and maintain activity. For example, Quistad et al. (1984, *Life Sci.*, 34:569–576) found that proctolin was rendered inactive in the gut whereas Raina et al. (1994, *J. Insect Physiol.*, 40:393–397) recently showed that approximately 5% of orally administered pheromone biosynthesis activating neuropeptide (PBAN) entered the hemolymph through the gut wall and stimulated production of sex pheromone. Although some insects that ingested PBAN did produce pheromone, the results were variable.

The contents of each of the above-mentioned publications are incorporated by reference herein.

SUMMARY OF THE INVENTION

We have discovered novel pseudopeptide analogs of the insect pyrokinin neuropeptide family which possess biological activity mimicking that of the naturally occurring neuropeptides. By addition of a hydrophobic moiety to an active portion of the pyrokinin peptides, analogs are produced which exhibit an overall amphiphilic nature and which are capable of penetrating the insect cuticle while still retaining biological activity. The analogs may be used for insect control by disrupting the reproductive, developmental, and/or digestive processes normally regulated by pryrokinins in insects.

In accordance with this discovery, it is an object of this invention to provide novel compounds having biological activity mimicking that of the naturally occurring pyrokinin neuropeptides.

It is also an object of this invention to provide compounds which are bioactive mimics of pyrokinin neuropeptides that are capable of penetrating the insect cuticle and which are resistant to degradation.

Another object is to provide compounds which are bioactive mimics of pyrokinin neuropeptides and their use for controlling insect populations and which may be topically applied.

Other objects and advantages of the invention will become readily apparent from the ensuing description.

DETAILED DESCRIPTION OF THE INVENTION

In the following description, the nomenclature used to define the peptides and pseudopeptides is that specified by Schroder and Lubke ["The Peptides", Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The compounds of the invention are prepared by conjugating a hydrophobic moiety to a member of the pyrokinin/PBAN (or FXPRLa) insect neuropeptide family, or a bioactive portion thereof, to render the compound amphiphilic. These compounds are of the general Formula I:

$$R—X_1—Pro—Arg—Leu—NH_2 \qquad (I)$$

where $X_1$ is Gly, Ser, Thr, or Val. The R moiety incorporates the hydrophobic functionality which is effective to impart the amphiphilic nature to the molecule.

In a first preferred embodiment, the compound is a pseudotetrapeptide analog of the C-terminal pyrokinin core region. In this embodiment, a hydrophobic carborane moiety is incorporated as a replacement for the phenyl ring of the amino acid Phe of the C-terminal pentapeptide, Phe—$X_1$—Pro—Arg—Leu—$NH_2$. Specifically, o- or m-carborane conjugated to a short chain alkanoyl-acyl group is substituted for the Phe. Referring to Formula I, R may be shown as:

$$Cb—(CH_2)_n—C(O)—$$

where Cb is a carborane, and n is 1, 2 or 3.

In a second preferred embodiment, the pyrokinins or at least an active C-terminal portion thereof containing the C-terminal pentapeptide Phe—$X_1$—Pro—Arg—Leu—$NH_2$, are modified at their N-terminus by addition of a hydrophobic moiety which may be an aromatic amine or aromatic acid. A variety of aromatic amines and acids are suitable for use herein. Preferred acids include phenyl alkanoic, alkenoic or alkynoic acids such as 6-phenyl hexanoic acid and 9-phenyl nonanoic acid, while preferred amines include phenyl alkanoic, alkenoic or alkynoic amines such as 4-phenyl butyl amine. Without being limited thereto, examples of other suitable aromatic acids include 2-biphenylenecarboxylic acid, 9-anthracenecarboxylic acid, 9-fluoreneacetic acid, 1-fluorenecarboxylic acid, and 1-pyrenebutyric acid, while other suitable aromatic amines include 1-aminoanthracene, 6-amino-3,4-benzocoumarin, 2-amino-7-bromofluorene, 6-aminochrysene, 3-aminofluoranthene, 9-aminophenanthrene, and 1-pyrenemethylamine.

The analog of this second embodiment may be prepared from any member of the pyrokinin family of neuropeptides. A variety of these pyrokinins have been previously described and are suitable for use herein. As mentioned, the pyrokinin polypeptide to which the hydrophobic moiety is attached should include at least an active C-terminal portion containing the C-terminal pentapeptide Phe—$X_1$—Pro—Arg—Leu—$NH_2$, and may encompass the entire native pyrokinin polypeptide. However, the polypeptide should not be so large as to lose the hydrophobic character introduced by the hydrophobic moiety. Thus, particularly when preparing analogs of larger pyrokinins, such as the 33 amino acid Hez—PBAN of the corn earworm, *Heliothis zea* (Raina et al., U.S. Pat. No. 5,032,576, the contents of which are incorporated by reference herein), or Bom—PBAN of the silkworm, *Bombyx mori*, best results are achieved when only using a C-terminal portion of the molecule. Thus, without being limited thereto, the size of the polypeptide (including the above-mentioned C-terminal pentapeptide) is preferably less than or equal to about 10 to 12 amino acids. Conversely, the skilled practitioner will recognize that when using smaller pyrokinin neuropeptides, including but not limited to *Locusta migratoria* myotropin II (Lom—MT—II) (Glu—Gly—Asp—Phe—Thr—Pro—Arg—LeuNH$_2$) or the octapeptide leucopyrokinin (LPK) of the cockroach, *Leucophaea maderae* (Nachman et al., 1986, Biochem. Biophys. Res. Commun., 137:936–942, the contents of which are incorporated by reference herein), the entire polypeptide may be used.

The above-mentioned hydrophobic aromatic acids or amines may be conjugated to the pyrokinin peptide directly or through an optional spacer. Use of the spacer is preferred however, to minimize any steric hindrance of the active polypeptide portion of the compound by the hydrophobic moiety and inhibition of receptor binding. The structure of the spacer will vary with the particular hydrophobic group. Without being limited thereto, when the hydrophobic moiety is an aromatic acid, preferred spacers may be non-polar hydrocarbons having a free amino group and free carboxyl group, or relatively non-polar or uncharged α-amino acids, such as Ala or Gly. When using an aromatic amine as the hydrophobic moiety, preferred spacers are hydrocarbon diacids, such as succinic acid. Other specific spacers may be readily determined by the practitioner skilled in the art.

In summary, in accordance with the structure shown in Formula (I), the structure of R for the second embodiment may be shown as:

$R_1$—$L_n$—$X_2$—Phe— where $R_1$ is the hydrophobic moiety, n is 0 or 1, and L is the spacer. The group $X_2$ may be a bond, or an amino acid or polypeptide which is naturally contiguous to the C-terminal pentapeptide —Phe—$X_1$—Pro—Arg—Leu—NH$_2$.

The peptides and pseudopeptide analogs of this invention may be synthesized by any suitable method, such as exclusively solid-phase techniques, partial solid-phase techniques, fragment condensation, or classical solution addition. The peptides may also be synthesized by recently developed recombinant DNA techniques which may be utilized for large-scale use in the field with the purpose of controlling insect reproduction to prevent crop damage.

Synthesis by the use of recombinant DNA techniques, for the purpose of this application, should be understood to include the suitable employment of structural genes coding for the sequence as specified hereinafter. The synthetic peptides may also be obtained by transforming a microorganism using an expression vector including a promoter or operator, or both, together with such structural genes and causing such transformed microorganisms to express the peptide.

As stated above, the compounds of Formula I can be synthesized by methods well known to those skilled in the art of peptide synthesis, e.g., solution phase synthesis [see Finn and Hoffman, In "Proteins", Vol. 2, 3rd Ed., H. Neurath and R. L. Hill (eds.)., Academic Press, New York, pp. 105–253 (1976)], or solid phase synthesis [see Barany and Merrifield, In "The Peptides," Vol. 2, E. Gross and J. Meienhofer (eds.), Academic Press, New York, pp. 3–284 (1979)], or stepwise solid phase synthesis as reported by Merrifield [J. Am. Chem. Soc. 85: 2149–2154 (1963)], the contents of each of which are incorporated herein by reference. In the preferred embodiment, the pyrokinin polypeptides and the analogs may be synthesized using the same solid phase techniques described by Nachman et al. (1995, Reg. Peptides, 57:359–370) or Christensen et al. (1991, Proc. Natl. Acad. Sci., USA, 88:4971–4975), the contents of each of which are incorporated by reference herein.

The pseudopeptide analogs of Formula I mimic the biological activity of the naturally occurring pyrokinin neuropeptides and have demonstrated the ability to induce a physiological response following application to an insect. In a preferred embodiment, the pseudopeptide analogs are effective for the stimulation or induction of pheromone biosynthesis in Lepidoptera species. Furthermore, the carboranyl analogs have exhibited almost irreversible binding to the pyrokinin receptor site in some species. Thus, the compounds may be used for insect control by causing production of pheromone at inappropriate times in the insects life cycle, or in inappropriate amounts, thereby disrupting the normal reproductive cycle and lowering insect populations. In a modification of this protocol, the compounds may be applied continuously or semicontinuously, or they may be formulated in timed or continuous release carriers for sustained release over time. It is envisioned that application in this manner may lead to continuous low levels of pheromone release in the insects, disrupting species propagation by impairing the ability of males to locate females. Further still, compounds such as the carboranyl analogs which bind strongly to the insect's pyrokinin receptors, and thereby down-regulate them, may also result in depletion of pheromone precursers causing production of insufficient pheromone to attract mates.

In addition to their use in control strategies for stimulating pheromone production, it is envisioned that the pseudopeptide analogs of this invention may be used for insect control by other mechanisms as well. For instance, the compounds may mimic the ability of the pyrokinins to regulate the developmental processes of egg diapause and pupariation, as well as oviduct contraction (influencing egg laying). Application of the compounds may disrupt these processes or even result in the laying of unfertilized eggs. Alternatively, the compounds may stimulate hindgut contraction in insects and consequently cause premature voiding of digestive contents and nutrients. Further still, application of the compounds may disrupt cuticular melanization, or accelerate pupariation. The compounds appear to be particularly suited for control of insects of the order Dictyoptera and Orthoptera, especially cockroaches and locusts, by these mechanisms, causing gut and oviduct contraction when applied to thereto. When administered to flies of the order Diptera, such as the fleshfly *Sarcophaga bullata*, the compounds effect the organism by another mechanism, accelerating pupariation. Thus, the compounds may also be used for the control of Dipteran pests, with application or ingestion of the compounds causing receptor down-regulation and disruption of the pupariation process and subsequent development.

As a practical matter it is anticipated that compositions of the pseudopeptide analogs would be prepared by formulating the compounds with an agriculturally acceptable inert carrier, particularly a solvent suitable for topical applications. Although a variety of solvents may be used, water is preferred. The compounds may also be formulated with solid inert carriers such as talc, clay or vermiculite, or incorporated into conventional controlled release microparticles or microcapsules.

The pseudopeptide analogs of this invention may be applied directly to the target insects (i.e., larvae, pupae and/or adults), or to the locus of the insects. Because the compounds will penetrate the insect cuticle, they are preferably administered topically, such as by direct spraying on the insect or a substrate which is likely to be contacted by the insect. Alternatively, the compounds may also be administered either subcutaneously, percutaneously, or orally. When they are to be ingested, they should be applied with their carrier to the insect diet. The compounds are administered in an amount effective to induce the desired response. For example, where the desired effect is stimulation of pheromone synthesis, an "effective amount" is defined to mean those quantities which will result in a significant increase in production of pheromone in a test group as compared to an untreated control. The actual effective amount will of course vary with the specific compound, the target insect and its stage of development, the application technique, the desired effect, and the duration of the effect, and may be readily determined by the practitioner skilled in the art. By way of illustration, we have found that when topically applying the carboranyltetrapeptide and 6-phenylhexanoic Lom—MT—II analogs of Examples 1 and 2, maximal pheromone stimulation is achieved by using concentrations of 60 and 100 picomoles/insect, respectively. However, although higher concentrations will not stimulate higher levels of pheromone, they will prolong the duration of the stimulation. Without being limited thereto, it is generally envisioned that the compounds should be topically applied in an amount greater than or equal to about 50 picomoles/insect. When the compounds are to be orally ingested or injected, the effective amounts may be significantly reduced. For example, the carboranyl analog accelerated pupariation at concentrations as low as 0.25 picomoles/insect when it was injected into fleshfly larvae.

The compounds encompassed herein are effective for controlling a broad spectrum of insects. Without being limited thereto, pests of particular interest are agronomically or commercially important insects, especially those of the orders Lepidoptera, Dictyoptera, Diptera, and Orthoptera. It is envisioned that the compounds will be particularly effective for controlling the corn earworm, the tobacco budworm, tobacco hornworm, cockroaches, grasshoppers, crickets, locusts, and cyclorrhaphous flies, such as the fleshfly.

The following examples are intended only to further illustrate the invention and are not intended to limit the scope of the invention which is defined by the claims.

EXAMPLE 1

Materials and Methods
Pseudopeptide Synthesis

Cbe or 2-o-carboranylethanoic acid was synthesized according to a previously described procedure (Radel and Kahl, 1993, *Amino Acids*, 5:170, the contents of which are incorporated by reference herein). The pyrokinin pseudotetrapeptide analog was synthesized by condensation of Cbe to the Thr—Pro—Arg(Pmc)—Leu—Rink Amide resin complex with 1 equivalent of a 1,3-diisopropylcarbodiimide/1-hydroxy-7-azabenzotriazole mixture in dimethylsulfoxide for 4 hours according to previously described procedures. The Thr—Pro—Arg(Pmc)—Leu—Rink Amide resin complex was synthesized via FMOC methodology as previously described (Nachman et al., 1995, *Peptides*, 16:809–813, the contents of which are incorporated by reference herein). Protected amino acid starting materials were purchased from Advanced Chemtech (Louisville, Ky.). The crude product was cleaved from the resin by stirring the resin complex with a mixture of trifluoroacetic acid (95%), anisole (5%), thioanisole (4%) and 1,2-ethanedithiol (1%) for 1 hour at RT. The resin was filtered and volatile reagents were removed in vacuo on a Savant Speed Vac concentrator at 40° C. The product was purified on a Waters C18 Sep Pak cartridge and a Delta Pak C18 reverse-phase column on a Waters Model 510 HPLC controlled with a Millenium 2010 chromatography manager system (Waters, Milford, Mass.) with detection at 214 nm at ambient temperature. Solvent A=0.1% aqueous trifluoroacetic acid (TFA); Solvent B=80% aqueous acetonitrile containing 0.1% TFA. Conditions: Initial solvent consisting of 20% B was followed by Waters linear program 6 to 100% B over 40 min; flow rate 2 ml/min. Retention time of carboranyl pseudotetrapaptide Cbe—Thr—Pro—Arg—Leu—$NH_2$: 21.5 min. The pure pseudotetrapeptide was analyzed and quantitated via amino acid analysis under previously described procedures (Nachman et al., 1995, *Peptides*, 16:809–813), revealing the following analyses: L(1.0), P(1.0), R(0.9) and T(1.0). Fast atom bombardment (FAB) mass spectra were obtained by adding 10 μg of pseudopeptide to glycerol (1.5 μl) on a copper probe, followed by bombardment with 8 KV Xe atoms on a Kratos MS-50 mass spectrometer (Kratos, Manchester, UK). The structural identity was confirmed by the presence of the following molecular ions ($MH^+$): Cbe—Thr—Pro—Arg—Leu—$NH_2$, 685.7 (Calcd. $MH^+$: 685.52). The molecular ion revealed an ion distribution consistent with the presence of 10 boron atoms.

Cockroach Myotropic Bioassay

*Leucophaea maderae* cockroaches were taken from stock colonies maintained at 27° C. and fed dry dog food ad lib. Cockroach hindguts, free of central nervous system (CNS) tissue, were dissected, immersed in saline, and prepared for recording of myogenic activity as previously described (Holman et al., 1991, ibid). Threshold concentrations were determined for each analogue by adding a known quantity of peptide (dissolved in 0.5 ml bioassay saline) to the bioassay chamber containing the hindgut and observing the response on a Gould 2200S oscillograph recorder. The quantity of the peptide analogues was calculated from the values obtained for Phe and/or Leu in the amino acid analysis. The threshold concentration was defined as the minimum concentration of peptide in the chamber required to evoke an observable change in the frequency (50%) or amplitude of contractions (5%) within 1 min and sustained for 3 min. Threshold concentrations were obtained from five cockroach hindguts on 5 consecutive days for each peptide. Quantitative data for dose-response plots were obtained as previously described (Holman et al., 1991, ibid).

*Heliothis virescens* Insects

Pupae of *H. virescens* were obtained from a laboratory colony maintained at the Insect Attractants, Behavior and Basic Biology Research Laboratory, USDA-ARS, in Gainesville, Fla. The pupae were separated by sex and the males were discarded. After eclosion, the females were held in 4-1 cages and provided with cotton wicks soaked with 5% sucrose solution. The insects were held at 25°±2° C, 65±3% relative humidity with a 12:12 (L:D) photoperiod. Virgin females were used for bioassays 2 and 3 days after eclosion during the 7th–8th hour of the photophase when endogenous levels of pheromone are very low (Abernathy, 1995, Regulation of sex pheromone production and oviposition in virgin females of noctuid moths, doctoral dissertation, University of Florida, Gainesville, Fla., pp. 1–107).

Pheromonotropic Assay (Injection)

Pheromone biosynthesis neuropeptide from *H. zea* (Hez—PBAN) and the carboranyl pseudopeptide Cbe—

Thr—Pro—Arg—Leu—NH$_2$ were dissolved in physiological saline (Christensen et al., 1991, *Proc. Natl. Acad. Sci. USA*, 88:4971–4975). Female *H. virescens* insects were injected through the side of the third abdominal segment using a 26-ga needle with 20 µl of the above solutions. Each female received a dose of 0.01, 0.03, 0.1, 0.3, 1, 3, 10, 30, 100 or 300 pmol. After 1 h of incubation, the terminal abdominal segments, which contain the pheromone gland, were excised and placed in 10 µl of hexane containing 10 ng each of internal standards (octadecane and nonadecane) used for quantitation and calculation of relative retention indices. The pheromone gland extracts were analyzed for the amount of (Z)-11-hexadecenal (Z11-16:AL), the major sex pheromone component of *H. virescens* (Klun et al., 1980, *J. Chem. Ecol.*, 6:165–175) by capillary gas chromatography. Hewlett-Packard 5890 gas chromatographs were equipped with splitless injectors, flame ionization detectors, and 30 m×0.25 mm (i.d.) fused silica "SPB 10" (polar) or "SPB1" (apolar) columns (Supelco). Conditions of chromatography were as follows: initial temperature=60° C.; injector operated in the splitless mode for 0.5 min; oven temperature increased by 30° C./min after 1 min; final temperature=190° C. ("SPB10") or 200° C. ("SPB1"); helium carrier gas at a linear flow velocity of 18 cm/s. A Nelson Analytical 3000° acquisition system (Cupertino, Calif.) was used to collect and analyze the data (Teal et al., 1989, *Proc. Natl. Acad. Sci. USA*, 86:2488–2492).

After the dose response of Hez—PBAN was completed, the 2 pmol dose was chosen to use for comparison with the carboranyl pseudopeptide assayed here. Insects were also injected with saline alone as a control. The pseudopeptide was prepared by dilution with saline as described above. Based on the dose-response for the activity of Hez—PBAN, six doses were chosen to assess the pheromonotropic activity of the carboranyl pseudopeptide. Females were injected with 20 µl containing 0.01, 0.03, 0.1, 0.3, 1, 3, 10, 30, 100, or 300 pmol. Each bioassay consisted of one dose of several different peptides along with saline and Hez—PBAN controls. The amount of pheromone present in extracts of the pheromone glands of females from each group was compared with that produced by females injected with 5 pmol of Hez—PBAN during that particular bioassay. After all the bioassays were completed, the amount of pheromone produced by each insect was calculated as a percentage of the amount of pheromone produced by females treated with Hez—PBAN. Data were analyzed using one-way ANOVA and t-test with "STATVIEW" software. Variability was reported as SEM.

Pheromonotropic Assay (Topical)

The amphiphilic carboranyl analog Cbe—Thr—Pro—Arg—Leu—NH$_2$ was dissolved in water and solutions at concentrations of 5, 10, 25, 60, and 200 pmol/µl were prepared. The cuticular scales along the lateral side of the abdomen were removed with a 1 ml plastic pipet tip attached to house vacuum with a rubber hose. A low vacuum was applied to the apparatus and the pipet tip was gently passed over the cuticle until the scales were drawn by suction. After the scales were removed, 1 µl of peptide solution was applied to the surface of the cuticle and smoothed evenly over the prepared surface. The insects were allowed to incubate 1 hour and then the pheromone gland was excised and the amount of pheromone determined by the method described above for the injected insects.

Results

Figure 1:
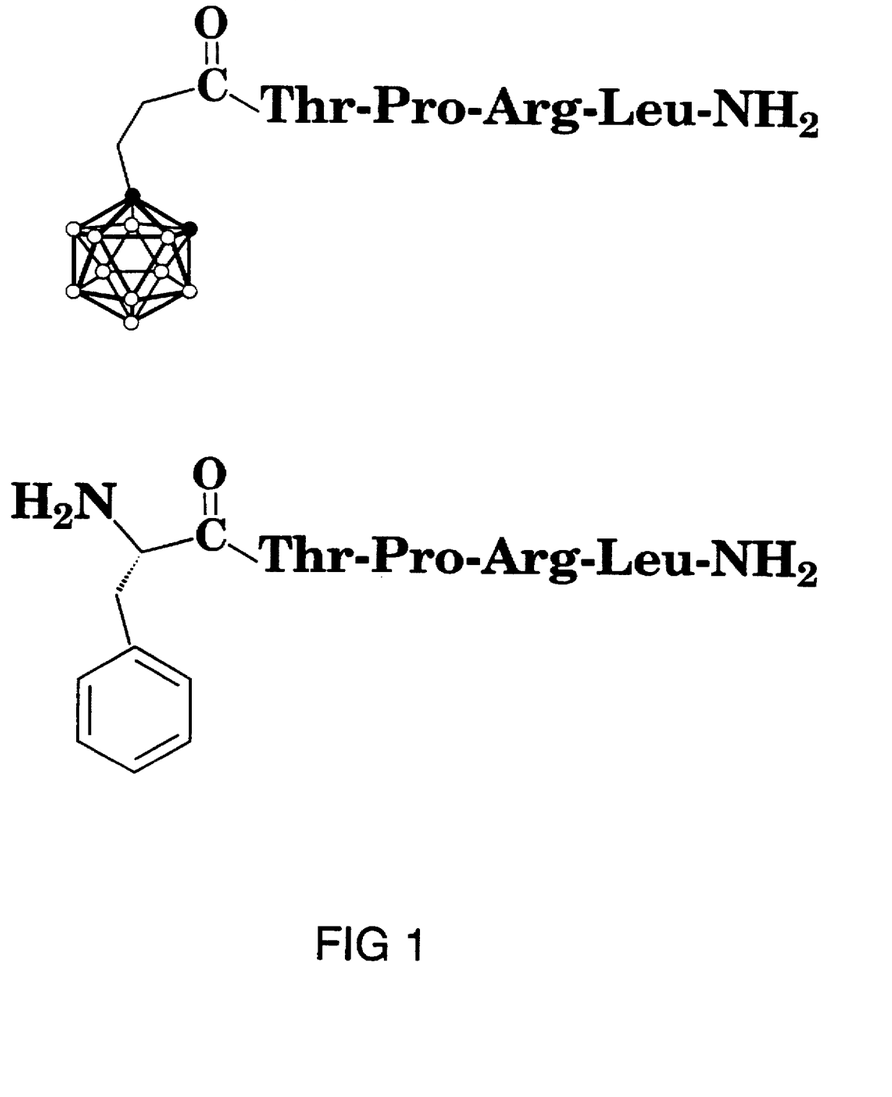
FIG. 1 shows the structure of the carboranyl pseudotetrapeptide analog prepared in Example 1 (above) where the phenyl ring of the Phe sidechain of the insect pyrokinin C-terminal pentapeptide core (below) is replaced with the cage-like or ball-shaped, hydrophobic carborane moiety.
Figure 2A:
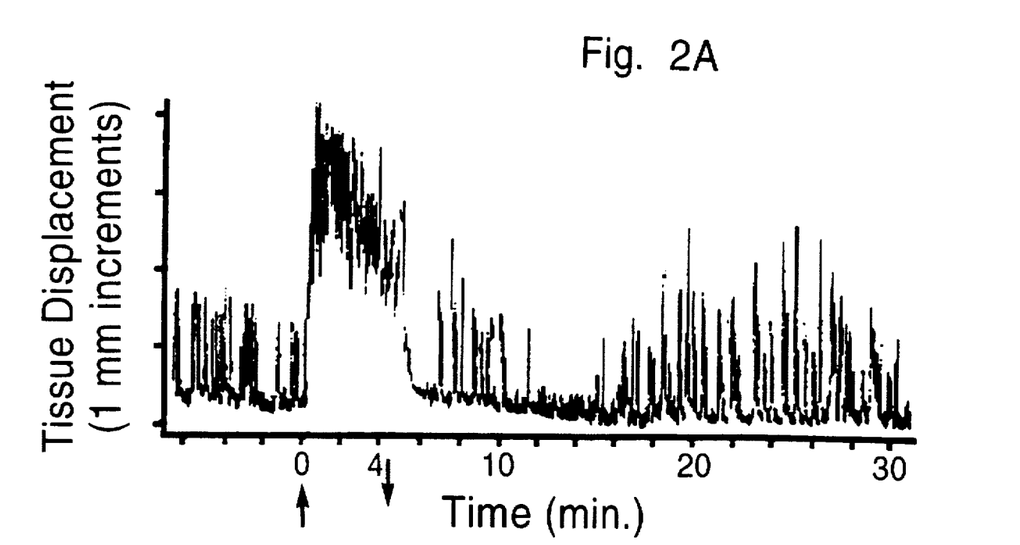
FIG. 2 is a graph, described in Example 1, showing that the stimulation of spontaneous contractions of the isolated cockroach hindgut elicited by the endogenous peptide LPK is immediately reversed by a saline rinse (above). In contrast, the myostimulatory response elicited by the carboranyl pseudotetrapeptide cannot be reversed by one or more saline rinses (below). The myostimulatory activity elicited by the pseudopeptide analog gradually subsides over about 20 minutes, presumably as a result of down-regulation of the receptor. The up arrow indicates the point of application of the test peptide solution and the down arrow signifies the saline rinse.
Figure 2B:
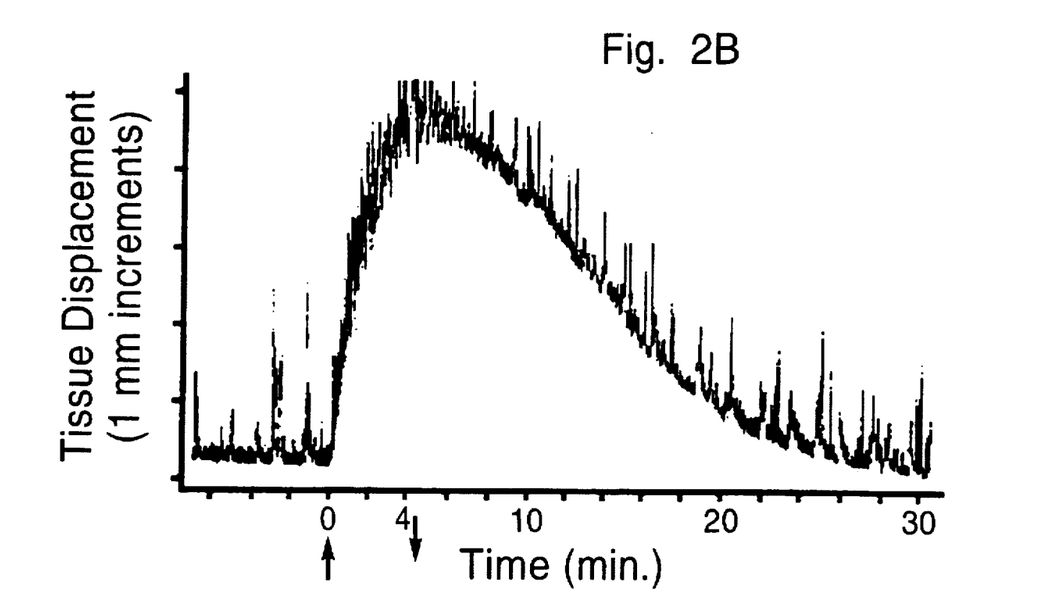

The carboranyl pseudotetrapeptide analog Cbe—Thr—Pro—Arg—Leu—NH$_2$ (Cbe=2-o-carboranylethanoyl or Cb—CH$_2$—CH$_2$—C(O)— [Cb=o-carborane]) (FIG. 1) of the pyrokinin/PBAN family demonstrates potent activity on an isolated *Leucophaea maderae* cockroach hindgut bioassay at a threshold concentration of 70 pM, over 30X and 10X more potent than the parent pentapeptide core Phe—Thr—Pro—Arg—Leu—NH$_2$ and the 8-mer LPK, respectively. While LPK and its fragments demonstrate reversible stimulation of contractions of the isolated cockroach hindgut, the potent myostimulatory activity of the carboranyl analog could not be reversed even following repeated saline rinses (FIG. 2). The myostimulatory activity arising from LPK immediately vanished following a saline rinse, whereas that from the pseudopeptide appeared irreversible and only gradually subsided over a 20 minute period to reach a resting state. This slow reduction of myostimulatory activity probably proceeds via down-regulation of the receptor.

Figure 3:
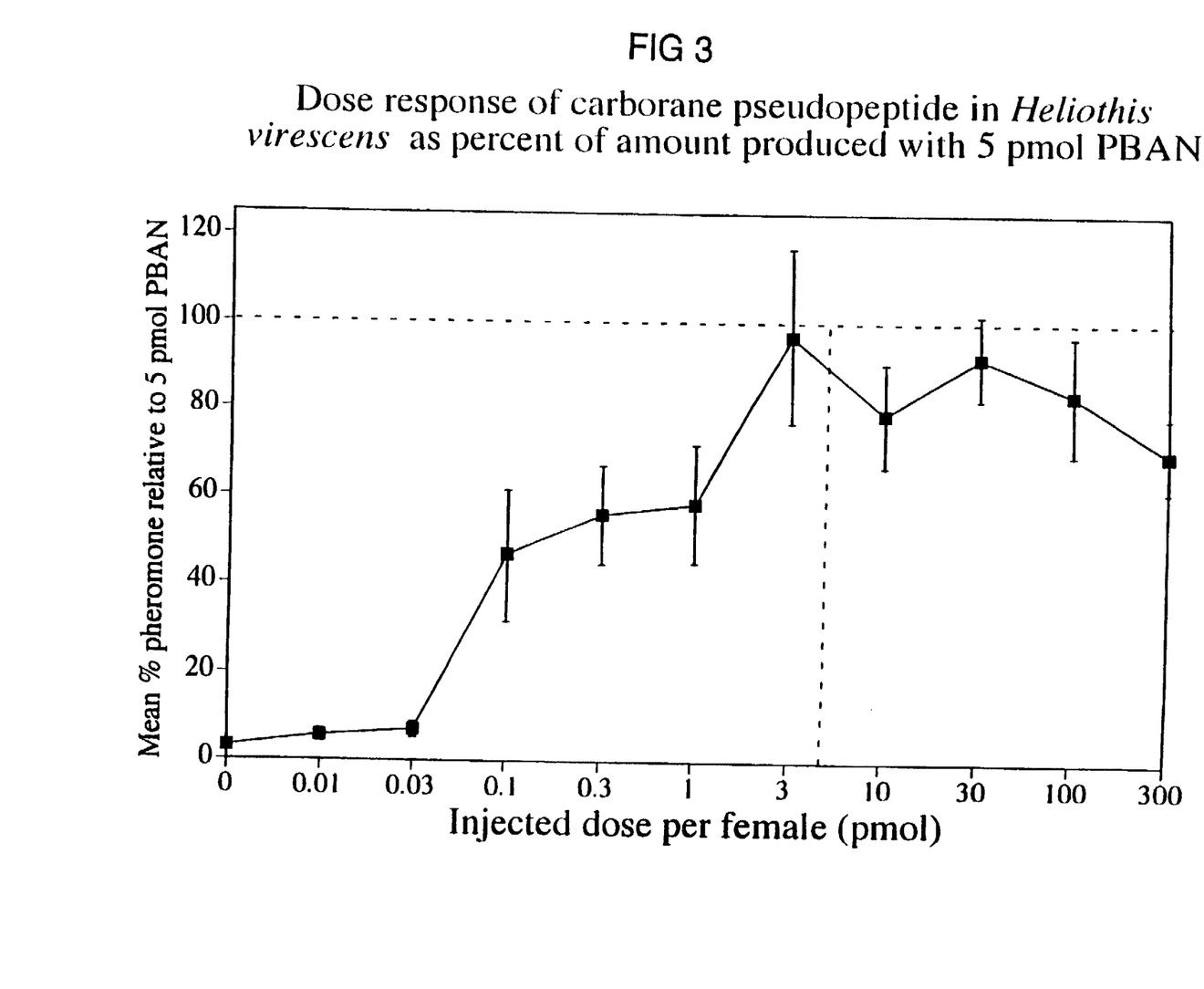
FIG. 3 shows the effect of dose of carborane pseudopeptide on stimulation of pheromone production when injected into virgin females of H. virescens. Pheromone glands were excised and extracted 60 min after injection of the pseudopeptide. The amount of pheromone produced in response to each dose is expressed as a percentage of the amount of pheromone produced by females injected with 5 pmol of synthetic Hez—PBAN, the optimal dose for stimulation of pheromone production. Dashed lines represent the response (100%) from the 5 pmol dose of Hez—PBAN used for that particular bioassay. Values are means of 8 replicates per dose (±SEM).
Figure 4:
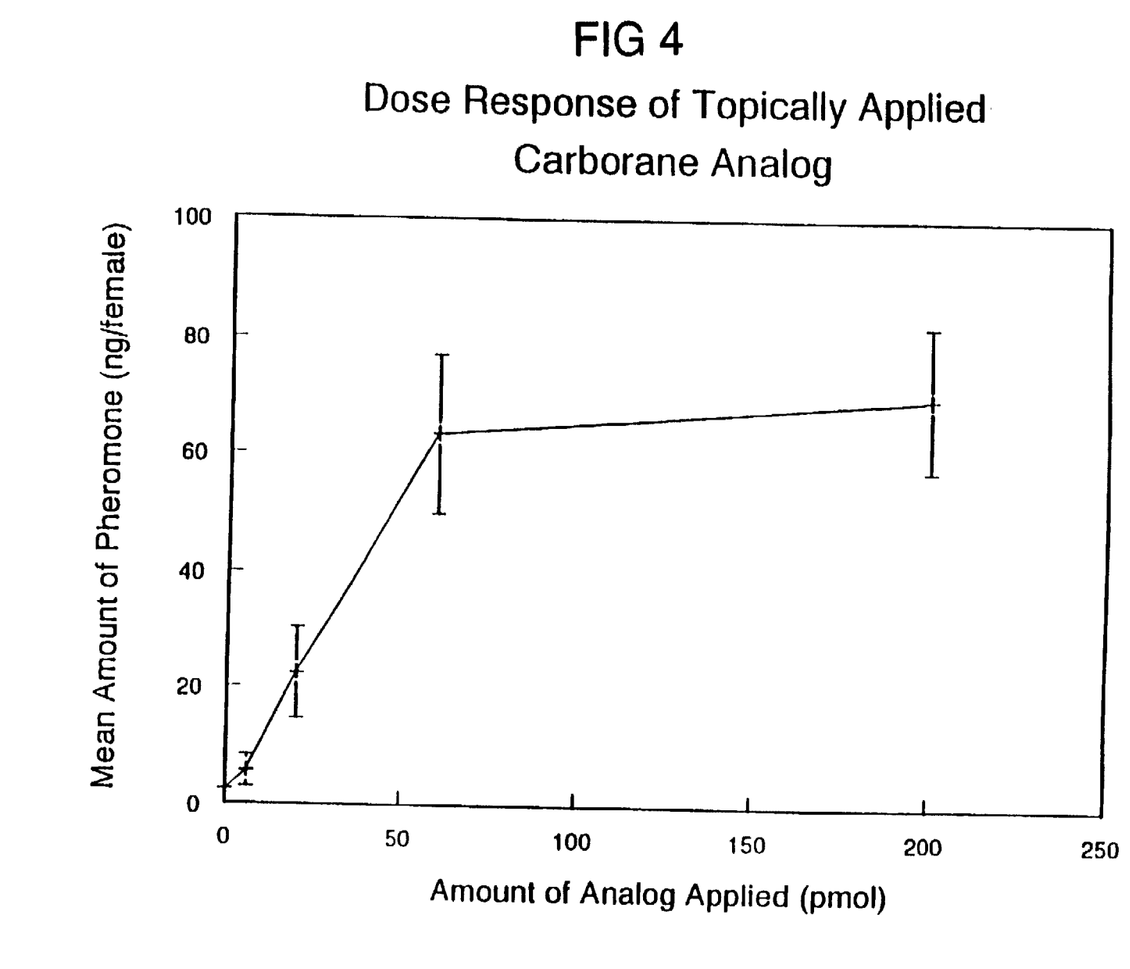
FIG. 4 shows the effect of dose of carborane pseudopeptide applied topically in 1 µl of $H_2O$ on production of pheromone by virgin females of H. virescens. Pheromone glands were excised and extracted 60 min after application of the pseudopeptide. Values are means of 10 replicates per dose (±SEM), except for 6 pmol (n=5).

The pseudopeptide analog also elicited pheromone production following injection into the female tobacco budworm moth *Heliothis virescens*. Dose-response data (FIG. 3) reveal that the small analog demonstrated an ED$_{50}$ of 0.1 pmoles/female and elicits a 100% response at 2.5 pmoles/female, equipotent with the 33-membered PBAN molecule endogenous to Helicoverpa. By contrast, the pyrokinin pentapeptide core fragment Phe—Thr—Pro—Arg—Leu—NH$_2$ elicits a truncated maximal response in the related moth *H. zea* of only 30% of the pheromone titre of PBAN at a larger dose of 70 pmoles/female. In another comparison, an 1800 fold greater dose of the pyrokinin pentapeptide core is required to achieve a 30% pheromonotropic titre in *H. zea* than for HezPBAN in *H. zea* or for either the carboranyl analog or HezPBAN in *H. virescens*. No data exists for pheromone production of the pentapeptide core fragment in *H. virescens*, but a comparison of existing dose-response data for the two moths suggests that the response profile is similar (Abernathy et al., 1995, *Peptides*, 16:215–219; Abernathy, 1995, ibid; Teal et al., 1993, *Canadian Entomol.*, 125:355–366). Dose-response data for pheromone production following topical application of the amphiphilic carboranyl analog in a 1 µl volume of aqueous solution to the lateral abdominal surface of H. virescens is illustrated in FIG. 4. The pseudopeptide analog elicits pheromone production at an ED$_{50}$ of 25 pmoles/female and approaches a 100% maximal response at 60 pmoles/female 15 minutes following topical application to the surface of the moth. Topical application of aqueous solutions of PBAN at a 100 pmole dose does not lead to production of statistically different levels of pheromone production in *H. virescens* over a control group at 15 min, 1 hr, 2 hr and even 3 hr following treatment (Abernathy, 1995, ibid).

Discussion

The carboranyl pseudotetrapeptide analog Cbe—Thr—Pro—Arg—Leu—NH$_2$ features a replacement of the phenyl ring of the Phe residue of the C-terminal pentapeptide core region Phe—Thr—Pro—Arg—Le—NH$_2$ of the pyrokinin/PBAN insect neuropeptide family. The dodecahedral volume created by rotation of the planar phenyl ring over 360° is mimicked by the ball-shaped or cage-like carborane structure (FIG. 1). It is capable of mimicking the aromatic character of the phenyl ring, but is a considerably more hydrophobic moiety (Varadajaran and Hawthorne, 1991, *Bioconjugate Chem*, 2:242–253). The greater surface area and hydrophobic character provided by the carboranyl cage moiety in comparison with the planar phenyl group may explain the irreversible nature of the myostimulatory response on the isolated cockroach hindgut (FIG. 2) elicited by this pseudopeptide analog. Although the hindgut myostimulation induced by the cockroach pyrokinin LPK subsides immediately following a saline rinse, the myostimulatory effects of the carboranyl analog cannot be reversed even following repeated saline rinses. Probably as a consequence of down-regulation of the receptor, the myostimulatory effect only slowly subsides over a period of more than 20 minutes following the rinse. The strong receptor-binding characteristics observed for this pseudopeptide make it unique among analogs of the pyrokinin/PBAN peptide family. The pseudopeptide demonstrates potent activity on the isolated *Leucophaea maderae* hindgut bioassay with a threshold response at 70 pM, 30X and 10X more active than the C-terminal pentapeptide core and the endogenous 8-membered LPK, respectively. When this small tetrapeptide analog is injected into the female tobacco budworm moth *Heliothis virescens*, it can elicit pheromone production with an $ED_{50}$ of 0.1 pmoles/female, 10 fold more potent than the much larger 33-membered HezPBAN peptide. The potent characteristics of the pseudopeptide analog in the in vivo pheromonotropic assay are likely due in part to its blocked N-terminus, which would protect it from aminopeptidase attack. HezPBAN is not blocked at the N-terminus. However, the isolated (in vitro) hindgut is suspended in a saline solution and the effect of dissolved peptide samples occurs virtually instantaneously following introduction into the chamber. Relative potency of sample peptide analogs in this assay, therefore, is largely due to receptor interaction characteristics rather than peptidase enzyme stability. Yet the carboranyl analog is 10X more potent than the N-terminally blocked cockroach pyrokinin LPK. Thus, the potency of this analog is probably also due to its strong receptor binding and/or interaction characteristics. The potency and efficacy observed for this small fragment analog demonstrates that the C-terminal pentapeptide core region of the natural pyrokinins, regardless of sequence length, contains all the structural information necessary to fully activate the receptor sites. Naturally occurring pyrokinin peptides form a dynamic equilibrium between a bound and a solution state in the hemolymph, where they can be inactivated by both soluble and tissue-bound peptidases. The carboranyl analog is conceivably afforded greater protection from encounters with peptidases by virtue of its propensity to remain in a receptor-bound state. Carboranyl analogs of insect neuropeptides represent an alternate class of analogs that can avoid peptidase attack. While traditional analog strategies involve the incorporation of peptidase resistant components into natural peptide sequences, carboranyl analogs can potentially avoid inactivation by peptidases because of strong receptor binding characteristics.

The presence of the hydrophobic carborane moiety coupled with the hydrophyllic, positively charged Arg residue confers amphiphylic properties to the pseudopeptide analog. Aqueous solutions of the carboranyl peptide readily "wet" the lateral abdominal surface of female *H. virescens*. These topically applied analog solutions also elicit pheromone production after about 15 minutes with an $EC_{50}$ of 25 pmoles/female and a maximal response at about 60 pmoles/female. In contrast, 100 pmole doses of HezPBAN in aqueous solution at 15 min, 1 hr, 2 hr, and 3 hr following topical application led to no statistical increase in pheromone production (Abernathy, 1995, ibid). The ability of the analog to transmigrate through the cuticular surface of the moth means that female moths can be induced to produce pheromone without using invasive procedures such as injection. Therefore, the carboranyl analog can potentially serve as a useful tool to insect researchers studying aspects of reproduction, endocrinology and behavior of not only *H. virescens* and *zea* but a wide range of moth species. For example, PBAN was used as a tool in the identification of the pheromone components of *Plodia interpunctella* (Teal et al., 1995, *J. Chem. Ecology*, 21:787–799). Injection of PBAN has also been used to study the biosynthetic pathways for pheromones (Fang et al., 1995, *Insect Biochem. Mol. Physiol.*, 25:39–48). The carboranyl analog could replace PBAN in situations such as these and be delivered in a noninvasive manner.

EXAMPLE 2

Methods and Materials
Insect Cultures:

Pupae of *Heliothis virescens* were obtained from a laboratory colony maintained at the Insect Attractants Behavior and Basic Biology Research Laboratory. USDA-ARS, Gainesville, Fla. The pupae were separated by sex and the females were held in 4–1 cages. Cages were inspected daily for newly eclosed adults which were transferred to new cages and provided with cotton wicks soaked with a 5% sucrose solution. The insects were held at 25°±20° C. and 65%±3% relative humidity with a 12:12 (L:D) photoperiod. Virgin females were used for bioassays 2 and 3 days after eclosion during the 7th–8th hour of the photophase when little or no pheromone is present in the gland (Teal et al., 1993, *Can. Entomol.*, 153:355–366). The cuticular scales were removed from the lateral side of the abdomen using a plastic pipet tip attached to house vacuum using a rubber hose. A low vacuum was applied and the pipet tip was passed gently over the cuticle until the scales were drawn off by suction. Insects were returned to the incubator for 24 h after the scales were removed for most experiments. However, insects were not given a recovery period in studies in which peptides were applied in DMSO (see below).

Peptide Synthesis:

Both Hez—PBAN and Lom—MT—II were synthesized using standard solid-phase methods as described elsewhere (Christensen et al., 1991, *Proc. Natl. Acad. Sci. USA*, 88:4971–4975; and Nachman et al., 1995, *Regul. Peptides*, 57:359–370, the contents of each of which are incorporated by reference herein). The N-terminally modified 6-phenylhexanoic acid (6 Pha) analog of Lom—MT—II ([6—Pha—Ala°]Lom—MT—II) was synthesized by coupling 6—Pha to the N-terminus of the Ala—Glu—Gly—Asp—Phe—Thr—Pro—Arg—Leu—Rink Amide peptide complex with 1 equivalent of a mixture of 1,3diisopropylcarbodiimide/1-hydroxy-7-azabenzotriazole in dimethyl sulfoxide for 4 h at room temperature. The crude peptide was cleaved from the resin anchor and protecting groups removed by treatment with a mixture of trifluoroacetic acid (TFA) (90%), anisol (5%), thianisol (4%) and 1,2-ethanedithiol (1%) for 1 h at RT. The resin was filtered and volatile reagents removed in vacuo on a Savant Speed Vac concentrator at 40° C. The product was purified on a Waters C18 Sep Pak cartridge followed by reversed phase liquid chromatography on a Delta Pak C18 reversed phase column using a Waters Model 510 HPLC controlled with a Millenium 2010 chromatography manager system with detection at 214 nm at ambient temperature. Solvent A was 0.1% aqueous TFA and solvent B was 80% aqueous acetonitrile containing 0.1% TFA. Conditions of chromatography were: initial solvent consisting of 20% B followed by Waters linear program 6 to 100% B over 40 min; flow rate=2 ml/min. The retention time of [6—Pha—Ala°]Lom—MT—II was 30.5 min. The pure pseudopeptide was analyzed and quantitated by amino acid analysis using previously described procedures (Nachman et al., 1995, *Regul. Peptides*, 57:359–370), revealing the following analysis: Ala (0.9), Arg (0.8), Asp (0.7), Glu (0.8), Gly (1.0), Leu (1.0), Phe (1.0), Pro (1.0) and Thr (1.0). Fast atomic bombardment mass spectra were obtained by adding 10 µg of pseudopeptide to glycerol on a copper probe, followed by bombardment with 8 Kv Xe atoms on a Kratos MS-50 mass spectrometer. The structural identity was confirmed by the presence of the following molecular ion (MH+): |6—Pha—Ala°|Lom—MT—II: 1178.5 (calculated MH+: 1178.62). Both Hez—PBAN and Lom—MT—II were purified using similar reversed phase liquid chromatographic techniques and the structures were confirmed by fast atomic bombardment mass spectroscopy. Analytical HPLC was performed with a Vidac 218TP (octadecyl-silica) reversed phase column (25 cm×0.46 cm) using 0.1% aqueous TFA (solvent A) and 0.1% TFA in acetonitrile (solvent B). Conditions of chromatography were: initial solvent consisting of 5% B followed by a linear program to 80% B over 75 min; flow rate=1 ml/min. Under these conditions the retention times for Lom—MT—II, Hez—PBAN and |6—Pha—Ala°| Lom—MT—II were 23.60±0.21, 28.54±0.19 and 39.31±0.20 min (n=5), respectively.

Pheromonotropic Activity of Injected Peptides:

The pheromonotropic activity of Hez—PBAN, Lom—MT—II and |6—Pha—Ala°|Lom—MT—II was first determined by a series of injection bioassays. Peptides were dissolved in physiological saline (Christensen et al., ibid) and diluted to concentrations of 0.003, 0.01, 0.03, 0.1, 0.3, 1.0, 3.0 and 10.0 pmol/µl. Insects were injected through the side of the 3rd abdominal segment using a 26 ga. needle with 20 µl of the above solutions. Thus, each female received a dose of 0.06, 0.2, 0.6, 2.0, 6.0, 20.0, 60.0, or 200.0 pmol. After 1 hour of incubation, the pheromone gland was excised and placed in 10 µl of hexane containing 10 ng each of heptadecane and nonadecane as internal standards to extract the pheromone components. Extracts were analyzed for the amount of (Z)-11-hexadecenal (Z11–16: Al), the major component of the sex pheromone blend by capillary gas chromatography equipped with both polar ("SPB 10") and apolar phase ("SPB1") columns using previously described conditions and methods (Teal et al., 1989, ibid). Data were analyzed using a one-way anova and Fisher's least significant difference test or a t-test with "INSTAT" software (GraphPad Software, 1993, "INSTAT", Graphpad Software Inc., San Diego, Calif.).

Topical Application of Peptides:

In initial studies we used dimethyl sulfoxide (DMSO) as a carrier to deliver Hez—PBAN or |6—Pha—Ala°|Lom—MT—II for topical applications. Peptides were dissolved at concentrations of 10, 50, 100, 500 and 1000 pmol/µl and 1 µl of peptide solution was applied to the surface of the cuticle using a Micro-10 plastic pipet. We also assessed different carrier solvents for their ability to deliver these two peptides. Peptides were dissolved at a concentration of 500 pmol/µl in: DMSO, water, or 80% acetonitrile:20% water. Solutions were applied to the descaled abdomen in 1 µl of solvent as above. The insects were allowed to incubate for 1 h prior to excision and extraction of the pheromone gland. Extracts were analyzed for the amount of pheromone as above.

The use of water as a carrier for |6—Pha—Ala°|Lom—MT—II was also assessed in dose response and temporal activity studies. For dose response studies |6—Pha—Ala°| Lom—MT—II was dissolved in water at concentrations of 5, 10, 25, 50, 75, 100, 250, 500, 750 and 1000 pmol/µl. Insects were incubated for 60 min after application of 1 µl of solution to the descaled abdomen. In temporal activity studies a 100 pmol/µl dose was selected. For these experiments insects were incubated for periods of 15, 30, 60, 120, or 180 min after application of 1 µl of solution to the descaled abdomen. The ability of the parent peptide, Lom—MT—II, to stimulate pheromone production when applied topically in water was assessed by applying doses of 50, 100, 250 and 500 pmol to the abdomen. Control treatments for this experiment included insects treated with only water and females treated by topical application of 100 pmol of |6—Pha—Ala°|Lom—MT—II. After incubation the sex pheromone glands were excised, extracted and analyzed for the amount of pheromone.

Results

Figure 5:
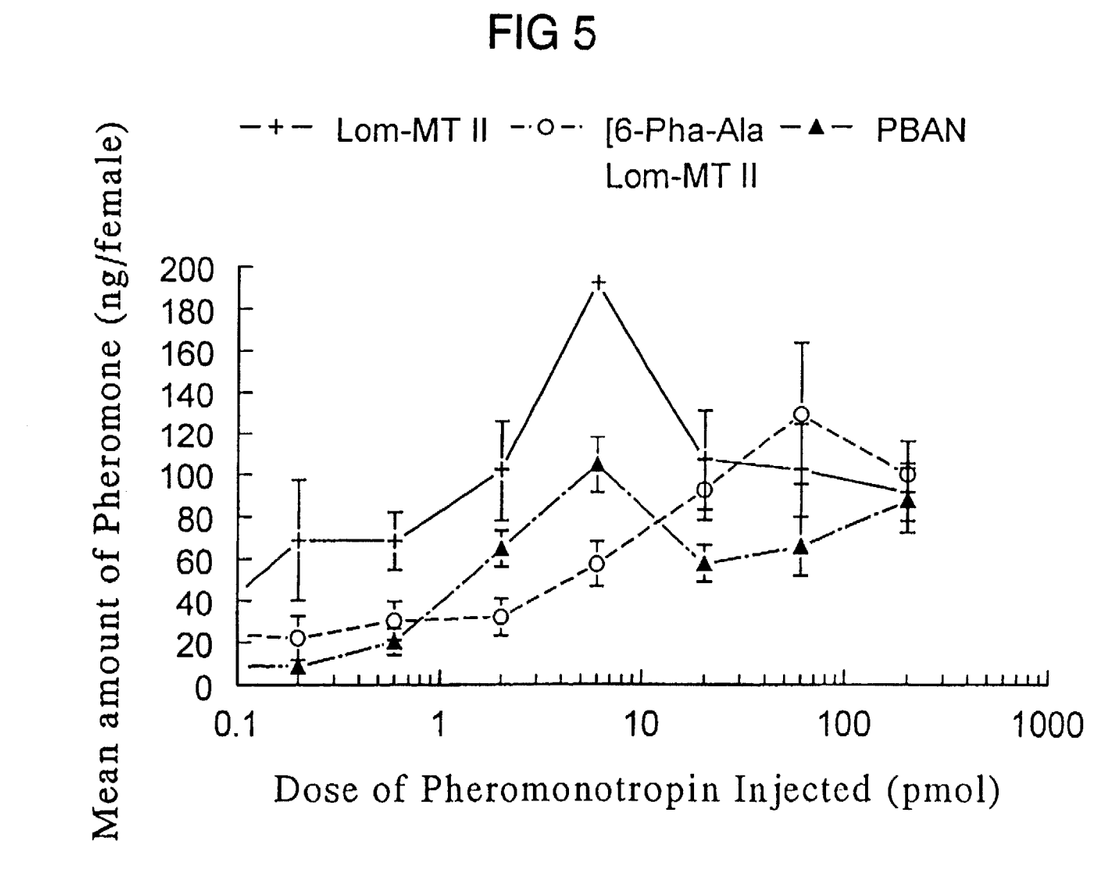
FIG. 5, described in Example 2, shows the amount of pheromone present in extracts obtained from females of H. virescens 60 min after injection of different doses of Lom—MT—II, or [6—Pha—Ala°]Lom—MT II or Hez—PBAN (n=8/treatment, ±SEM).

Pheromonotropic Activity of |6—Pha—Ala°|Lom—MT—II:

Dose response studies indicated that the base peptide from which |6—Pha—Ala°|Lom—MT—II was derived, Lom—MT—II, had greater activity than Hez—PBAN at all but the highest dose when injected into females of *H. virescens* (FIG. 5). The addition of 6-phenylhexanoic acid-Ala to the parent peptide (Lom—MT—II) reduced the activity, compared to Lom—MT—II, at doses up to 6 pmol, but responses were equivalent to Hez—PBAN at all other doses. At the highest doses of 60 and 200 pmol/µl, all three peptides induced production of equivalent amounts of pheromone (F (5,33)=1.01, p=0.378) when injected into females (FIG. 5).

Figure 6:
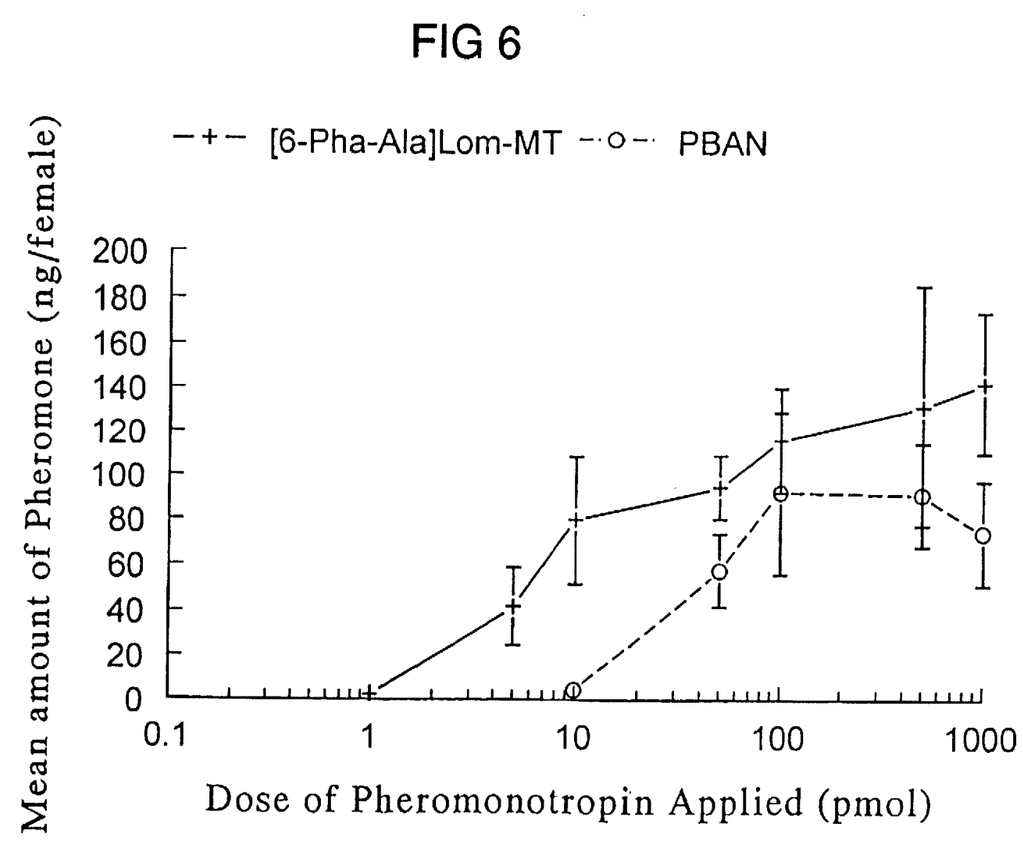
FIG. 6 shows the amount of pheromone present in extracts obtained from females of H. virescens 60 min after topical application of different doses of either [6—Pha—Ala°] Lom—MT—II or Hez—PBAN dissolved in DMSO (n=5/treatment, ±SEM).

Topical Application of Peptides:

Insects treated topically with |6—Pha—Ala°|Lom—MT—II or Hez—PBAN in DMSO produced pheromone (FIG. 6). However, insects treated with Hez—PBAN did not produce pheromone until a dose of 50 pmol/female was applied. In contrast, insects treated with |6—Pha—Ala°| Lom—MT—II produced pheromone in response to topical application of 5 and 10 pmol doses. At doses from 100 to 1000 pmol/female insects treated with |6—Pha—Ala°| Lom—MT—II and Hez—PBAN produced equivalent amounts of pheromone (F (Raina, 1993, ibid; and Nachman et al., 1995, *Regul. Peptides*, 57:359–370)=0.61, p=0.69).

Figure 7:
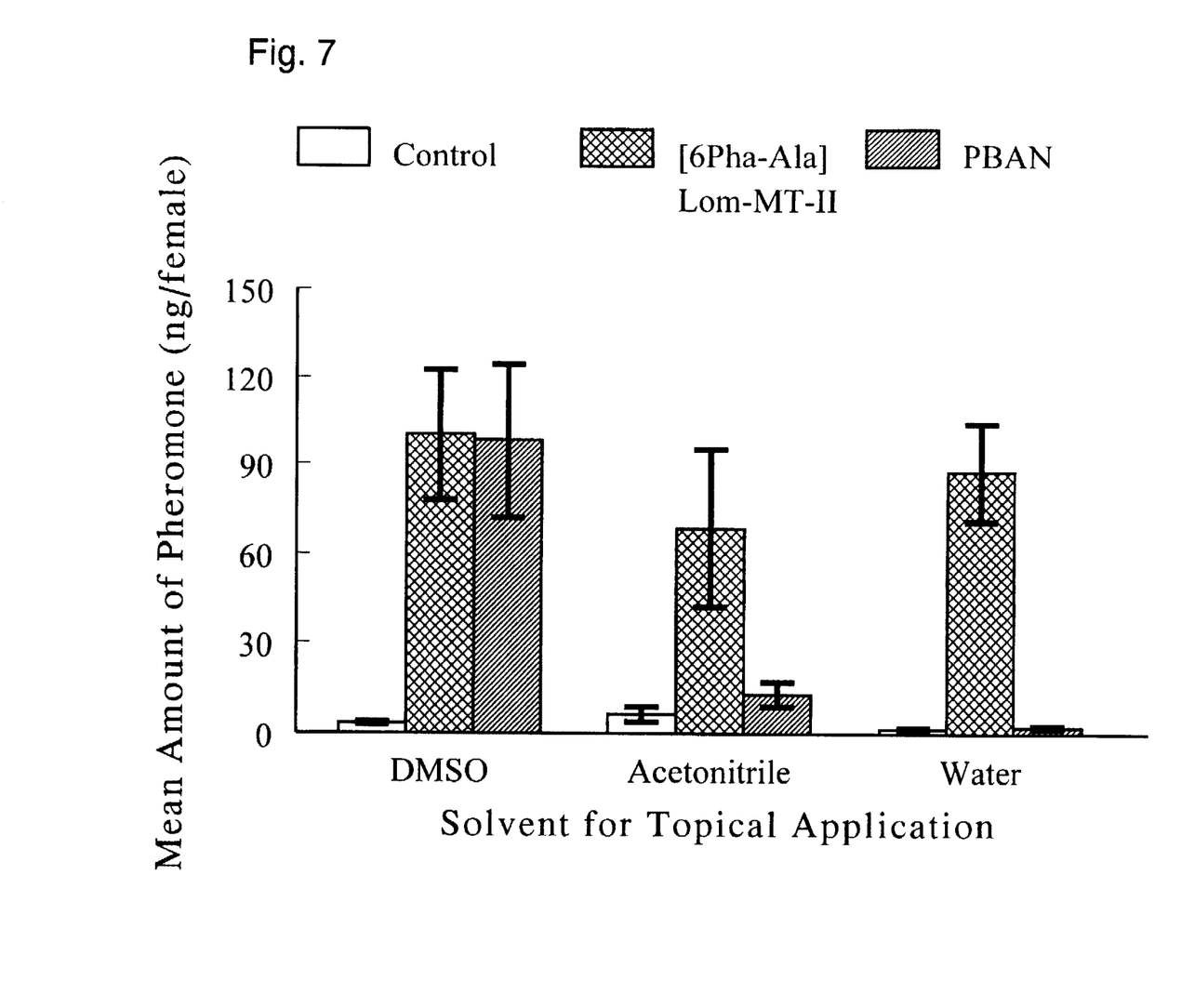
FIG. 7 shows the amount of pheromone present in extracts obtained from females of H. virescens 60 min after topical application of 500 pmol of either [6—Pha—Ala°]Lom—MT—II or Hez—PBAN dissolved in DMSO, water, or 80% acetonitrile in water compared with amounts of pheromone present in extracts from females treated with only solvents (n=5/treatment, ±SEM).

One dose (500 pmol/female) was chosen to compare different solvents for topical application. DMSO, and 80% acetonitrile flowed easily over the cuticle but water tended to ball up due to the wax layer of the cuticle. As expected, both Hez—PBAN and |6—Pha—Ala°|Lom—MT—II stimulated production of equivalent amounts of pheromone when applied in DMSO (FIG. 7). Hez—PBAN showed no significant activity when applied in either 80% acetonitrile or water. However, |6—Pha—Ala°|Lom—MT—II stimulated production of significant amounts of pheromone when applied in either 80% acetonitrile or only water.

Figure 8:
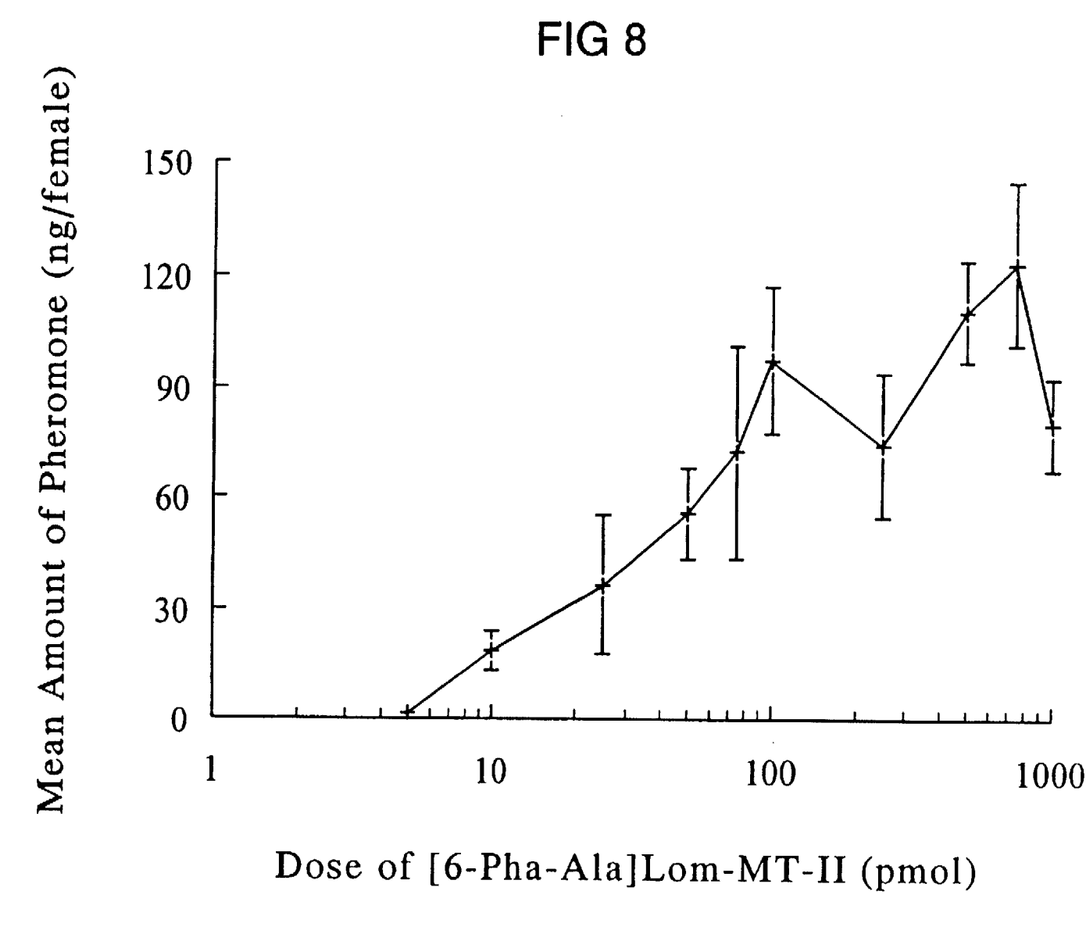
FIG. 8 shows the amount of pheromone present in extracts obtained from females of H. virescens 60 min after topical application of different doses of [6—Pha—Ala°]Lom—MT—II applied in water (n=8/treatment, ±SEM)
Figure 9:
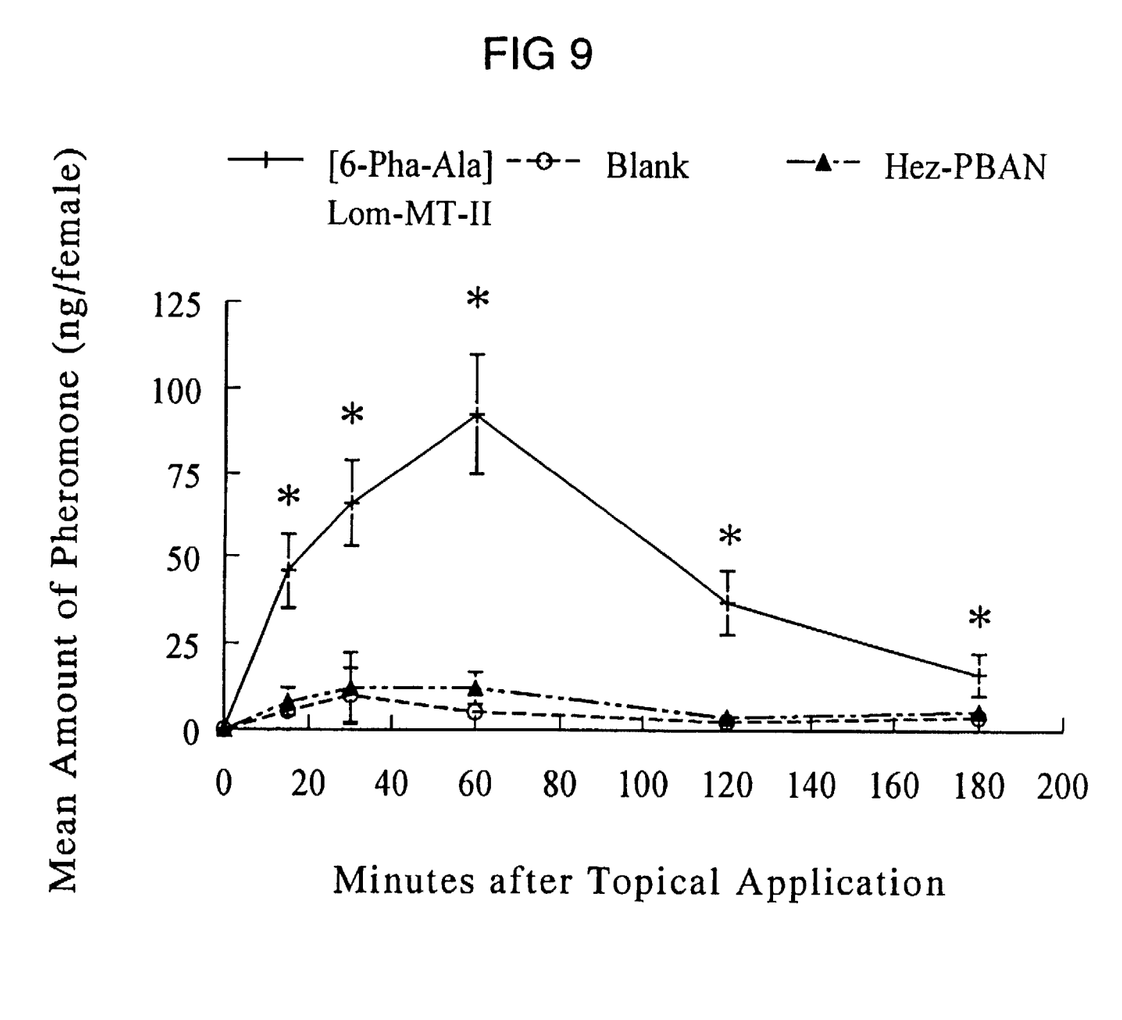
FIG. 9 shows the amount of pheromone present in extracts obtained from females of H. virescens at different time intervals after topical application of water or 100 pmol of either [6—Pha-Ala°]Lom—MT—II or Hez—PBAN dissolved in water (n=10, ±SEM). Means for [6—Pha—Ala°] Lom—MT—II superscribed with a * are significantly different from extracts obtained either water controls or Hez—PBAN treated insects in a Fisher's LSD test, α=0.05. Extracts obtained from Hez—PBAN treated insects were no different from controls at any time interval.
Figure 10:
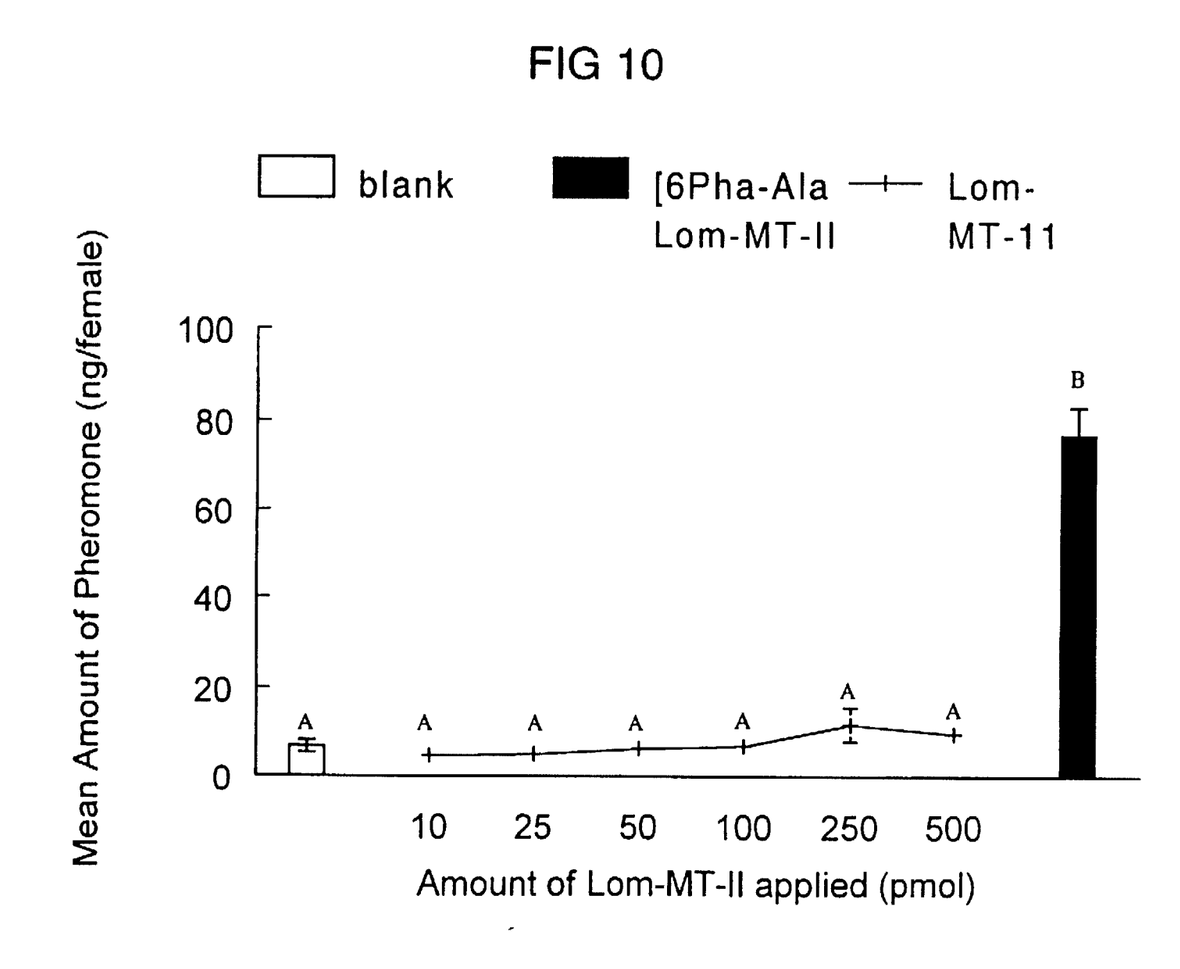
FIG. 10 shows the amount of pheromone present in extracts obtained from females 60 min after treatment by topical application of different amounts of Lom—MT—II in water compared with amounts of pheromone present in extracts from insects treated with just water or 100 pmol of [6—Pha—Ala°]Lom—MT—II. Means (n=10/treatment, ±SE) superscribed by the same letter are not significantly different in a Fisher's LSD test, α=0.05.

Topical application of |6—Pha—Ala°|Lom—MT—II in water stimulated production of significantly more pheromone than just water when applied at doses of 10 pmol (t (18)=2.6, p=0.018) and above (FIG. 8). The activity increased in a linear fashion to 100 pmol (r=0.98), but doses from 100–1000 pmol were not different (F(4, 36)=0.94, p=0.453). Time response studies (FIG. 9) showed that extracts of pheromone glands contained significant amounts of pheromone in as little as 15 min after application of 100 pmol of |6—Pha—Ala°|Lom—MT—II. The activity of the peptide was maximal at 60 min after application and declined gradually during the subsequent 120 min. Extracts obtained from insects in studies where Hez—PBAN was applied in water for the same time periods did not contain more pheromone than was present in extracts obtained from insects treated with water only (FIG. 9). Similarly, no insects treated by topical application of Lom—MT—II at doses of 10–500 pmol in water produced significantly more pheromone than was present in extracts obtained from insects treated with just water (FIG. 10). However, insects treated with pheromone than females treated with any dose of Lom—MT—II (FIG. 6).

Discussion

Results of our study indicate that Lom—MT—II is a more potent pheromonotropin than Hez—PBAN when injected into females of *H. virescens*. Similar results were found in studies using *Helicoverpa zea* (Abernathy et al., 1995, ibid). That study indicated that substitution of the variable Xxx position of the C-terminal active core (Phe—Xxx—Pro—Arg—Leu—amide) by Thr imparted more potent pheromonotropic activity to the peptide than substitution by Ser, the amino acid in the Xxx position of all PBANs identified to date. Alteration of Lom—MT—II by addition of the hydrophobic moiety, 6-phenylhexanoic acid—Ala, to the N-terminus yielded the pseudopeptide, |6—Pha—Ala°| Lom—MT—II. This mimic had pheromonotropic activity equivalent to Hez—PBAN (FIG. 5). These results demonstrate that the N-terminus of pyrokinin-like neuropeptides can be altered with nonpeptide moieties and retain pheromonotropic activity.

We chose DMSO as an initial solvent for topical application studies because of its ability to dissolve compounds having a wide range of polarities. In fact, DMSO is commonly used as a carrier solvent to apply pheromone precursors for studies on pheromone biosynthesis in moths (see Bjostad et al., 1987, In: *Pheromone Biochemistry*, Prestwich and Blomquist, eds., Academic Press, Orlando, Fla., pp. 77–117). Both Hez—PBAN and |6—Pha—Ala°|Lom—MT—II were effective in stimulating pheromone production when applied to the surface of the descaled cuticle in DMSO. Thus, application of DMSO solutions containing both PBAN, or |6—Pha—Ala°|Lom—MT—II, and pheromone precursors may provide a highly effective, non-invasive technique to study early events in biosynthesis of pheromones by moths.

The fact that ten fold more Hez—PBAN than |6—Pha—Ala°|Lom—MT—II was required to stimulate significant pheromone production when DMSO was used as a carrier solvent can not be explained by differential solubilities of the two compounds in DMSO. We believe that this difference reflects the fact that the lipidic 6-phenylhexanoic acid moiety allows |6—Pha—Ala°|Lom—MT—II to penetrate the wax layer of the cuticle more efficiently. Support for the hypothesis that |6—Pha—Ala°|Lom—MT—II penetrates the cuticle more efficiently than Hez—PBAN comes from the results obtained when using 80% acetonitrile in water as a solvent. Both PBAN and |6—Pha—Ala°|Lom—MT—II are soluble in this solvent system and both wetted the waxy surface of the cuticle equally well. Thus, equal amounts of the two pheromonotropins were applied to the cuticle. However, only |6—Pha—Ala°|Lom—MT—II induced the production of pheromone (FIG. 7). This result indicates clearly that only |6—Pha—Ala°|Lom—MT—II penetrated the cuticle. The highly polar nature of Hez—PBAN probably inhibited penetration of the apolar wax layer of the cuticular surface. However, the lipidic nature of |6—Pha—Ala°|Lom—MT—II, imparted by the N-terminal 6-phenylhexanoic acid moiety, gives this pseudopeptide amphiphilic properties. Thus, |6—Pha—Ala°|Lom—MT—II readily penetrated both the apolar wax layer and also the more polar protein and chitin layers of the cuticle. The amphiphilic nature of |6—Pha—Ala°|Lom—MT—II not only allows penetration of the cuticle but also allows it to be soluble in water and gives it surfactant properties. The surfactant properties reduce the surface tension between the cuticular surface and water so that solutions of the pseudopeptide can be easily applied to the surface of the cuticle. Water alone, or either PBAN or Lom—MT—II dissolved in water tended to ball up when applied to the cuticle because the surface tension permits little adherence to the waxy surface. This, plus the polar nature of PBAN and Lom—MT—II, which inhibits penetration of the waxy cuticular surface, explains why these two peptides failed to stimulate production of significant amounts of pheromone when applied to the surface of the cuticle in water.

|6—Pha—Ala°|Lom—MT—II represents a new class of synthetic insect neuropeptide mimetics capable of penetrating the insect cuticle when applied topically in water and inducing an endogenous response.

It is understood that the foregoing detailed description is given merely by way of illustration and that modifications and variations may be made therein without departing from the spirit and scope of the invention.

TABLE 1

Comparative activity of the carboranyl pyrokinin analog Cbe—Thr—Pro—Arg—Leu—NH$_2$ and natural pyrokinins in cockroach hindgut myotropic and Heliothis moth pheromonotropic bioassays

| | Myostimulation of the Isolated Cockroach (*Leucophaea maderae*) Hindgut Threshold Concentration[a](pM) | Pheromone Production in Female Tobacco Budworm Moth (*Heliothis virescens*) | | | |
|---|---|---|---|---|---|
| | | Via Injection | | Via Topical Application | |
| Peptide Analog | | ED$_{50}$ (pmoles) | Maximal Response[b] (pmoles) | ED$_{50}$ (pmoles) | Maximal Response[b] (pmoles) |
| Cbe—Thr—Pro—Arg—Leu—NH$_2$[c] | 70 | 0.1 | 2.5 | 25 | 60 |
| Phe—Thr—Pro—Arg—Leu—NH$_2$ | 2,200 (18) | 50[e,f] (2) | 70[e,f] (2) | — | — |
| pQTSPhe—Thr—Pro—Arg—Leu—NH$_2$ (leucopyrokinin[LPK]) | 650 (18) | 5[e] (2) | 70[e] (2) | — | — |
| HezPBAN[d] | 2,600 (20) | 1.0 (33) | 5.0 (33) | Inactive[g] | Inactive[g] |

[b]Maximal pheromone production relative to 5 pmoles PBAN via injection.
[c]Cbe = 2-o-carboranylethanoyl-.
[d]HezPBAN = LSDDMPATPADQEMYRQDPEQIDSRTKYPhe—Ser—Pro—Arg—Leu—NH$_2$.
[e]Data from the related corn earworm moth *H. zea*
[f]Maximal response is a truncated 30% of that elicited by HezPBAN.
[g]Topical application of aqueous solutions of HezPBAN at a 100 pmole dose does not lead to production of statistically different levels of pheromone production over a control group at 15 min, 1 hr, 2 hr, or even 3 hr following treatment.

We claim:

1. A compound of the formula

R—X₁—Pro—Arg—Leu—NH₂ wherein X₁ is selected from the group consisting of Gly, Ser, Thr, and Val, and R is:
- (a) Cb—(CH₂)ₙ—C(O)— and
  - (i) Cb is a carborane, and
  - (ii) n is 1, 2, or 3; or
- (b) R₁—Lₙ—X₂—Phe— and
  - (i) R₁ is a hydrophobic moiety selected from the group consisting of aromatic containing amine groups and aromatic containing acyl groups, said hydrophobic moiety being effective to render said compound amphiphilic,
  - (ii) n is 0 or 1,
  - (iii) L is a spacer which, when R₁ is an aromatic containing acyl group, is selected from the group consisting of non-polar hydrocarbon groups having an amino group and acyl group, and uncharged α-amino acids, or when R₁ is an aromatic containing amine group, said spacer is a diacyl group, and
  - (iv) X₂ is selected from the group consisting of a bond, an amino acid, and a polypeptide group, said polypeptide group comprising all or a portion of a pyrokinin neuropeptide which is naturally contiguous to the C terminal pentapeptide —Phe—X₁—Pro—Arg—Leu—NH₂, and which said polypeptide group is sufficiently small as to retain the hydrophobicity of said compound introduced by said hydrophobic moiety.

2. The compound of claim 1 wherein R is said Cb—(CH₂)ₙ—C(O)—.

3. The compound of claim 2 wherein said carborane is selected from the group consisting of o-carborane and m-carborane.

4. The compound of claim 1 wherein R is said R₁—Lₙ—X₂—Phe—.

5. The compound of claim 4 wherein X₂ is a bond.

6. The compound of claim 4 wherein X₂ is a polypeptide group having less than or equal to about 7 amino acids.

7. The compound of claim 6 wherein said polypeptide group is —Glu—Gly—Asp—.

8. The compound of claim 4 wherein R₁ is a hydrophobic aromatic containing acyl group, n is 1, and L is selected from the group consisting of non-polar hydrocarbon groups having a free amino group and free acyl group, and uncharged α-amino acids.

9. The compound of claim 8 wherein R₁ is selected from the group consisting of phenyl alkanoic acyl groups, phenyl alkenoic acyl groups, and phenyl alkynoic acyl groups.

10. The compound of claim 9 wherein R₁ is selected from the group consisting of a 6-phenyl hexanoic acyl group and a 9-phenyl nonanoic acyl group.

11. The compound of claim 8 wherein L is selected from the group consisting of Ala and Gly.

12. The compound of claim 4 wherein R₁ is a hydrophobic aromatic containing acyl group and n is 0.

13. The compound of claim 12 wherein R₁ is selected from the group consisting of phenyl alkanoic acyl groups, phenyl alkenoic acyl groups, and phenyl alkynoic acyl groups.

14. The compound of claim 13 wherein R₁ is selected from the group consisting of a 6-phenyl hexanoic acyl group and a 9-phenyl nonanoic acyl group.

15. A composition comprising the compound of claim 1 and an inert carrier.

16. The composition of claim 15 wherein said carrier is water.

17. A method for controlling insects comprising applying the compound of claim 1 to the locus of said insects.

18. The method of claim 17 wherein said insects are selected from the group consisting of insects of the order Lepidoptera, insects of the order Dictyoptera, insects of the order Diptera, and insects of the order Orthoptera.

19. The method of claim 17 wherein said applying comprises topically applying said compound onto said insects.

20. The method of claim 17 wherein said compound is applied in an amount effective to stimulate pheromone production by said insect.

21. The method of claim 17 wherein said compound is applied in an amount effective to stimulate gut contraction by said insect.

22. The method of claim 17 wherein said compound is applied in an amount effective to stimulate oviduct contraction by said insect.

* * * * *